United States Patent [19]

Tsujihara et al.

[11] Patent Number: 4,882,447
[45] Date of Patent: Nov. 21, 1989

[54] NOVEL ORGANIC PLATINUM COMPLEX AND PROCESS FOR THE PREPARATION THEREOF

[75] Inventors: Kenji Tsujihara, Urawa; Yoshihisa Arai, Funabashi; Osamu Ohtsuki, Nagaokakyo; Tadashi Nakatani, Takatsuki, all of Japan

[73] Assignee: Tanabe Seiyaku Co., Ltd., Osaka, Japan

[21] Appl. No.: 157,969

[22] Filed: Feb. 19, 1988

[30] Foreign Application Priority Data

Feb. 20, 1987 [JP] Japan .................................. 62-38240

[51] Int. Cl.$^4$ ................................................ C07F 9/68
[52] U.S. Cl. ........................................ 556/40; 556/137
[58] Field of Search .................... 514/492; 556/137, 40

[56] References Cited

U.S. PATENT DOCUMENTS

| | | |
|---|---|---|
| 4,115,418 | 9/1978 | Gale et al. |
| 4,551,502 | 11/1985 | Howell et al. ........................ 556/146 |
| 4,594,238 | 6/1986 | Berch . |
| 4,614,811 | 9/1986 | Gandolfi . |
| 4,665,210 | 5/1987 | Bitha et al. . |

FOREIGN PATENT DOCUMENTS

| | | |
|---|---|---|
| 0026813 | 4/1981 | European Pat. Off. . |
| 0111388 | 5/1984 | European Pat. Off. . |
| WO87/02364 | 4/1987 | PCT Int'l Appl. . |

Primary Examiner—John Doll
Assistant Examiner—Stuart L. Hendrickson
Attorney, Agent, or Firm—Birch, Stewart, Kolasch & Birch

[57] ABSTRACT

Novel organic platinum complex of the formula:

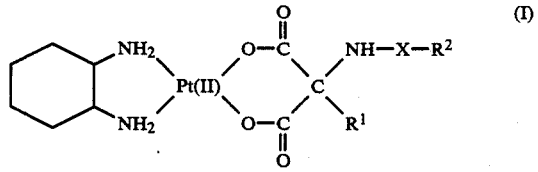

wherein $R^1$ is hydrogen atom or a lower alkyl group, $R^2$ is a substituted or unsubstituted lower alkyl group, a lower alkenyl group, a lower alkanoyl group, a mono- or di-lower alkylamino group, a substituted or unsubstituted nitrogen-containing hetero-monocyclic group, an oxygen-containing hetero-monocyclic group, or a group of the formula:
—$CH_2O(CH_2CH_2O)_mCH_3$, X is carbonyl group or sulfonyl group, m is an integer of 1 or 2,
which has excellent anti-tumor activity against various tumors and is useful as an anti-tumor agent, and a process for the preparation thereof, and a pharmaceutical composition containing said compound.

5 Claims, No Drawings

NOVEL ORGANIC PLATINUM COMPLEX AND PROCESS FOR THE PREPARATION THEREOF

This invention relates to a novel organic platinum complex and a process for the preparation thereof. More particularly, it relates to a novel organic platinum complex of the formula:

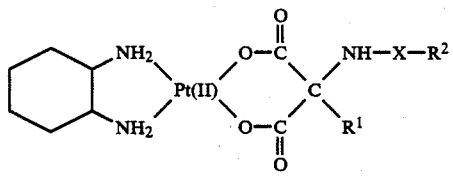

wherein
$R^1$ is hydrogen atom or a lower alkyl group,
$R^2$ is a substituted or unsubstituted lower alkyl group, a lower alkenyl group, a lower alkanoyl group, a mono- or di-lower alkylamino group, a substituted or unsubstituted nitrogen-containing hetero-monocyclic group, an oxygen-containing hetero-monocyclic group, or a group of the formula: $-CH_2O(CH_2CH_2O)_mCH_3$,
X is carbonyl group or sulfonyl group,
m is an integer of 1 or 2, and a process for the preparation thereof.

The organic platinum complex of this invention has an excellent anti-tumor activity and is useful as an anti-tumor agent.

TECHNICAL BACKGROUND

Since it has been found tht cisplatin [chemical name: cis-dichlorodiammine platinum (II)] has an anti-tumor activity [cf. Nature, Vol. 222, page 385 (1969)], there have been prepared many organic platinum complexes wherein various diamines are used as a ligand, and the anti-tumor activity of these compounds have also been studied. However, many of these known compounds show the anti-tumor activity against only a certain limited tumors and do not show sufficient anti-tumor effect. Further, although some of these known compounds show comparatively excellent anti-tumor activity, they have toxicity to kidney and the organ of hearing, or they have less solubility in water and hence are hardly prepared in a pharmaceutical preparation, or they are less easily transferred into organs in vivo [cf. Science, Vol. 192, page 774 (1976)]. Accordingly, most known compounds are not suitable for clinical use.

Accordingly, it has been desired to find novel organic platinum complex having excellent anti-tumor activity with less toxicity and with high water solubility.

SUMMARY DESCRIPTION OF THE INVENTION

An object of the invention is to provide a novel organic platinum complex which has excellent anti-tumor activity against various tumors with less toxicity and with high water solubility. Another object of the invention is to provide a process for the preparation of the organic platinum complex. A further object of the invention is to provide a pharmaceutical composition containing as an active ingredient said organic platinum complex which is useful as an anti-tumor agent. These and other objects and advantages of the invention will be apparent to those skilled in the art from the following description.

DETAILED DESCRIPTION OF THE INVENTION

The organic platinum complex of this invention has the formula (I) as set forth hereinbefore. The organic platinum complex is novel and has excellent anti-tumor activity against various tumors, particularly against solid tumors such as sarcoma 180, Ehrlich carcinoma, Yoshida sarcoma, and ascites hepatoma, and the like, and hence, it is useful to prolong the survival time of warm-blood animals, including human, afflicted with tumors, and/or minimize the growth of tumor cells in said animals. Moreover, the platinum complex is also effective against tumors such as leukemia L-1210, P388, and the like.

The organic platinum complex of the invention also has advantageous properties such as less toxicity to kidney, remarkedly higher water solubility and is easily transferred into organs in vivo in comparison with known organic platinum complexes. For instance, [2-(acetylamino)malonato](trans-l-1,2-diaminocyclohexane) platinum (II), when administered to mice at a dose required to induce 100% increase in the life span, showed no influences on the indices of renal functions such as the concentration of creatinine and ueas in blood; and said platinum compeex also has 20 time or higher water solubility than that of cisplatin.

Examples of the organic platinum complex of this invention includes those of the formula (I) wherein $R^1$ is hydrogen atom or a lower alkyl group; $R^2$ is (i) a lower alkyl group optionally having one or two substituent(s) selected from the group consisting of hydroxy group, nitro group, a lower alkoxy group, a lower alkylsulfinyl group, a 5- or 6-membered nitrogen-containing hetero-monocyclic group-substituted carbonyl group (e.g. morpholinocarbonyl group), and a 5- or 6-membered oxygen-containing hetero-monocyclic group-oxy (e.g. tetrahydropyranyloxy group), (ii) a lower alkenyl group, (iii) a lower alkanoyl group, (iv) a mono- or di-lower alkylamino group, (v) a 5- or 6-membered nitrogen-containing hetero-monocyclic group optionally having a substituent selected from oxo group and a lower alkoxy-lower alkanoyl group (e.g. 2-oxopyrrolidyl group, an N-(lower alkoxy-lower alkanoyl)pyrrolidyl group), (vi) a 5- or 6-membered oxygen-containing hetero-monocyclic group (e.g. furyl group, tetrahydrofuryl group), or (vii) a group of the formula: $-CH_2O(CH_2CH_2O)_mCH_3$; X is carbonyl or sulfonyl group; and m is 1 or 2.

Among them, the preferred subgenus includes the platinum complex (I) in which $R^2$ is a lower alkyl group, a hydroxy-lower alkyl group, a lower alkenyl group, furyl group or a group of the formula: $-CH_2O(CH_2CH_2O)_mCH_3$, and X is carbonyl group.

Most preferred subgenus includes the platinum complex (I) in which $R^2$ is a lower alyl group or a group of the formula: $-CH_2O(CH_2CH_2O)_mCH_3$, and X is carbonyl group.

In the platinum complex (I) of the present invention, the term "lower alkyl group" should be interpreted as referring to those of one to 6 carbon atoms, and the terms "lower alkenyl group" and "lower alkanoyl group" should be interpreted as referring to those of 2 to 6 carbon atoms; but alkyl groups of 1 to 3 carbon atoms, alkenyl groups and alkanoyl groups of 2 or 3 carbon atoms are usually exemplified as preferred examples of these groups.

In the organic platinum complex (I) of this invention, the one ligand 1,2-diaminocyclohexane has asymmetric carbons at 1- and 2-positions, and hence, there are three isomers [i.e. trans-l, trans-d, and cis-isomer (mesoform)]. The organic platinum complex of this invention includes the complex wherein these isomers, preferably trans-isomers, more preferably trans-l, are used as a ligand. Besides, in the organic platinum complex of this invention, another ligand 2-(substituted amino)malonate ion has an asymmetric carbon at 2-position, and hence, there are two optical isomers, and furthermore, owing to the asymmetric carbon in R² group and/or sulfinyl, there may be another optical isomer. The organic platinum complex of this invention includes also these complexes wherein any one of the isomers is used as a ligand or a mixture thereof.

The organic platinum complex of this invention can be prepared by reacting a 1,2-diaminocyclohexane platinum complex of the formula:

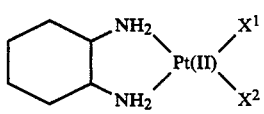
(II)

wherein X¹ and X² are a reactive residue, with a 2-(substituted amino)malonic acid of the formula:

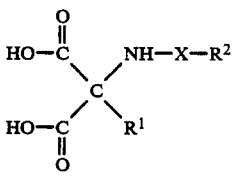
(III)

wherein R¹, R² and X are as defined above; or a salt thereof.

The 1,2-diaminocyclohexane platinum complex includes the compounds of the formula (II) wherein X¹ and X² are each, for example, nitrato, hydroxy, or a halogen (e.g. fluorine, chlorine, bromine, iodine), or are combined together to form sulfato group.

The reaction of the 1,2-diaminocyclohexane platinum complex (II) and the 2-(substituted amino)malonic acid (III) or a salt thereof can be carried out in water or an aqueous organic solvent (e.g. aqueous alkanol, aqueous acetone, etc.). For instance, in case of 1,2-diaminocyclohexane platinum complex (II) wherein X¹ and X² are each nitrato group or are combined together to form sulfato group, it is preferably reacted with an alkali metal salt (e.g. sodium or potassium salt) of the 2-(substituted amino)malonic acid (III). In case of the platinum complex (II) wherein X¹ and X² are each hydroxy, it is preferably reacted with a free 2-(substituted amino)malonic acid (III). These reactions proceed preferably at 20° to 40° C. Besides, in case of the 1,2-diaminocyclohexane platinum complex (II) wherein X¹ and X² are each a halogen atom, it is preferably reacted with a silver salt of 2-(substituted amino)malonic acid (III) at room temperature under light-protection.

The starting material (III) used in the above reaction can be prepared, for example, by reacting an amine compound of the formula:

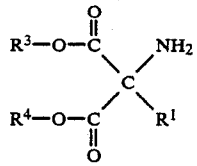
(IV)

wherein R¹ is as defined above, and R³ and R⁴ are the same or different and are each hydrogen atom or an ester residue, or a salt thereof with an acid compound of the formula:

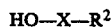
HO—X—R² (V)

wherein X and R² are as defined above, in the presence of a dehydrating agent, or alternatively by reacting an amine compound (IV) with a reactive derivative (e.g. an acid chloride) of an acid compound (V) in the presence of an acid scavenger, to give a compound of the formula:

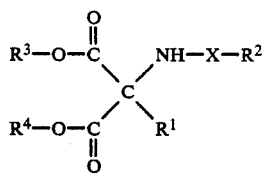
(VI)

wherein R¹, R², X, R³ and R⁴ are as defined above, and in case of R³ and/or R⁴ being an ester residue (e.g. a lower alkyl), followed by hydrolysis of the compound (VI) in a usual manner.

Among the starting materials, the compound of the formula (III) wherein R² is a mono-lower alkylamino and X is carbonyl may also be prepared by reacting an amine compound (IV) with a lower alkyl isocyanate, and the compound of the formula (III) wherein R² is a lower alkylsulfinyl-lower alkyl or a nitro-lower alkyl and X is carbonyl may also be prepared by reacting an amine compound (IV) with a lower alkylsulfenyl- or halogeno-lower fatty acid, followed by oxidation or nitration of the reaction product. The compound of the formula (III) wherein R² is a lower alkyl substituted by tetrahydropyranyloxy may also be prepared by reacting a compound (III) wherein R² is a hydroxy-substituted lower alkyl with dihydropyran in the presence of an acid, optionally followed by hydrolysis of the product.

Further, the starting compound (III) wherein R¹ is a lower alkyl group may be prepared by introducing a lower alkyl group at 2-position of the starting compound (III) wherein R¹ is hydrogen atom, according to a conventional method of malonic ester synthesis, if required, followed by hydrolysis of the product.

The starting material (III) or a salt thereof thus prepared can be used in the reaction with 1,2-diaminocyclohexane platinum complex (II) without isolation or after being isolated.

The organic platinum complex (I) of this invention has excellent anti-tumor activity against various tumors, and shows particularly excellent growth inhibition of solid tumors. Moreover, the organic platinum complex of this invention is also advantageous in the high water solubility by which it is easily prepared in a pharmaceutical preparation, and further easily transferred into organs in vivo.

Owing to these excellent properties, the organic platinum complex (I) of this invention is useful for the treatment of various tumors, such as prostate tumor, orchis tumor, ovary tumor, malignant lymphoma, leukemia, breast cancer, and the like.

The organic platinum complex (I) of this invention is highly soluble in water and can be administered by oral or parenteral route, preferably by parenteral route. The organic platinum complex (I) of this invention can be used for pharmaceutical use in the form of a pharmaceutical preparation suitable for either oral or parenteral administration. The pharmaceutical preparation includes solid preparations such as tablets, capsules, and the like, and liquid preparations such as solutions, suspensions, emulsions, and the like. When the organic platinum complex (I) is administered parenterally, it may be in the form of an injection or suppository, preferably an injection. The pharmaceutical preparations are prepared by a conventional method by admixing with a pharmaceutically acceptable carrier or diluent. Suitable pharmaceutically acceptable carrier or diluent includes, for example, gelatin, lactose, glucose, sodium chloride, starch, magnesium stearate, talc, vegetable oils, and the like. For injection, it is used in the form of an isotonic solution, which is prepared by admixing the compound (I) with an isotonic agent such as mannitol, sodium chloride, glucose, sorbitol, glycerol, xylitol, fructose, maltose, mannose, or the like. The pharmaceutical preparations may be sterilized and/or may contain auxiliaries such as preserving and stabilizing agents. The dose of the organic platinum complex (I) of this invention may vary depending on the administration routes, ages, weights and conditions of the hosts, the severity of the diseases, and the like, but it may usually be in the range of about 20 to 1,000 mg/m², preferably about 40 to 300 mg/m².

The present invention is illustrated by the following Experiment and Examples but should not be construed to be limited thereto.

EXPERIMENT

Chemotherapeutic effect of the organic platinum complex (I) of this invention was investigated as follows.

Sarcoma cells ($1.5 \times 10^6$ cells) were inoculated subcutaneously at inguinal region of a group of five female mice (ICR mice, five week age). Twenty four hours after the inoculation, a solution of test compound was intraperitoneally administered to the mice once a day for 5 days. The weight of tumor in the mice was measured 5 days after the administration. The results are shown in Table 1.

TABLE 1

| Compd. (a) Nos. | Dose (mg/kg/day) | Inhibition rate (%) (b) | Therapeutic index (MTD/ED30) (c) |
|---|---|---|---|
| Compounds of this invention | | | |
| 1 | 100 | Toxic (5/5) | 13.9 |
|  | 50 | 89.4 | (50/3.6) |
|  | 25 | 64.8 | |
|  | 12.5 | 52.3 | |
|  | 6.25 | 36.0 | |
|  | 3.12 | 28.4 | |
| 2 | 100 | Toxic (4/5) | 7.5 |
|  | 50 | 80.2 | (50/6.7) |
|  | 25 | 65.4 | |
|  | 12.5 | 57.6 | |
|  | 6.25 | 17.8 | |
| 3 | 100 | Toxic (5/5) | 7.1 |
|  | 50 | 80.7 | (50/7.0) |
|  | 25 | 63.5 | |
|  | 12.5 | 49.7 | |
|  | 6.25 | 26.4 | |

[Notes]:
(a) Compound Nos.    Chemical name
(Compounds of this invention)
1    [2-(acetylamino)malonato] (trans-l-1,2-diaminocyclohexane)platinum (II)
2    [2-[[(methoxyethoxy)acetyl]amino]malonato] (trans-l-1,2-diaminocyclohexane)platinum (II)
3    [2-(acetylamino)-2-methylmalonato] (trans-l-1,2-diaminocyclohexane)platinum (II)

(b) Inhibition rate (%) $= \dfrac{C - T}{C} \times 100$ wherein C = mean weight of tumor in the untreated mice
T = mean weight of tumor in the treated mice.

(c) MTD = the maximum tolerated dose.
ED30 = dose which showed 30% inhibition for the growth of tumor.

EXAMPLE 1

(1) Diethyl 2-[(hydroxyacetyl)amino]malonate (0.56 g) is dissolved in 1N aqueous sodium hydroxide (5 ml), and the mixture is reacted at room temperature for 10 hours, and thereafter, the reaction mixture is concentrated under reduced pressure. The residue is washed with methanol to give disodium 2-[(hydroxyacetyl)amino]malonate (0.51 g).

M.p. >250° C.

IR $\nu_{Max}^{Nujol}$ (cm$^{-1}$): 3400, 3300, 1650, 1620.

(2) To a solution of dinitrato(trans-l-1,2-diaminocyclohexane)platinum (II) (0.87 g) in water (30 ml) is added an aqueous solution (5 ml) of the product in the above (1) (0.51 g), and the mixture is allowed to stand at room temperature for 5 hours. The reaction mixture is adsorbed onto high porous resin HP-20 (manufactured by Mitsubishi Chemical Industries Limited). After washing the resin with water, the adsorbed product is eluted with methanol-water (1:1), and the eluate is concentrated under reduced pressure, and to the residue is added ethanol-acetone (1:1). The precipitate is separated by filtration and dried to give [2-[(hydroxyacetyl)amino]malonato](trans-l-1,2-diaminocyclohexane)platinum (II) (0.63 g) as pale yellow powder.

M.p. 235° C. (decomp.).

IR $\nu_{Max}^{Nujol}$ (cm$^{-1}$): 3400, 3220, 3120, 1670, 1650.

EXAMPLE 2

To a solution of dinitrato(trans-l-1,2-diaminocyclohexane)platinum (II) (0.87 g) in water (30 ml) is added an aqueous solution (5 ml) of disodium 2-(acetylamino)malonate [prepared from the corresponding diethyl ester in the same manner as described in Example 1-(1)] (0.45 g), and the mixture is allowed to stand at room temperature for 5 hours. The reaction mixture is concentrated under reduced pressure and cooled. The precipitate is separated by filtration, washed with cold water and ethanol and dried to give [2-(acetylamino)malonato](trans-l-1,2-diaminocyclohexane)platinum (II) (0.51 g) as pale yellow crystalline powder.

M.p. 238° C. (decomp.).
IR $\nu_{Max}^{Nujol}$ (cm$^{-1}$): 3300, 3210, 3070, 1680, 1640.

EXAMPLES 3 TO 28

In the same manner as described in Examples 1 or 2, the corresponding starting materials are treated to give complexes as shown in Table 2.

TABLE 2

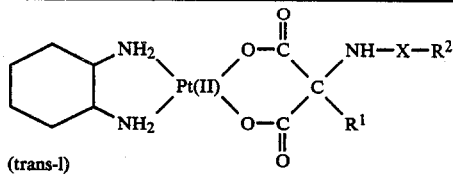

(I)

(trans-l)

(In Examples 3-26 & 28, X = CO, and in Example 27, X = SO$_2$, and in Examples 3-27, R$^1$ = H and in Example 28, R$^1$ = CH$_3$)

| Ex. No. | Complex (I)*$^1$ R$^2$ | M.p., etc. | IR $\nu_{Max}^{Nujol}$ (cm$^{-1}$) |
|---|---|---|---|
| 3 | —CH$_2$CH$_3$ | Pale yellow crystal. powder, m.p. >250° C. | 3310, 3220, 3080, 1680, 1640 |
| 4 | —CH=CH$_2$ | Pale yellow crystal. powder, m.p. >250° C. | 3280, 3220, 3080, 1680, 1640 |
| 5 | —NHCH$_3$ | Pale yellow powder, m.p. 247° C. (dec.) | 3350, 3220, 3080, 1690, 1640 |
| 6 | (l)-pyrrolidinone (5-yl) | Pale yellow powder, m.p. >250° C. | 3300, 3220, 3080, 1720, 1680, 1640 |
| 7 | —CH$_2$OCH$_3$ | Pale yellow powder, m.p. 240-242° C. (dec.) | 3420, 3230, 3100, 1670, 1640, 1110 |
| 8 | —CH(OH)CH$_3$ (dl) | Pale yellow powder, m.p. 215-220° C. (dec.) | 3350, 3220, 3080, 1680, 1640 |
| 9 | —CH(OH)CH$_2$OH | Pale yellow powder, m.p. 231° C. (dec.) | 3400, 3340, 3220, 3130, 1660, 1650 |
| 10 | —CH$_2$OCH$_2$CH$_2$—OCH$_3$ | Pale yellow powder, m.p. 210° C. (dec.) | 3380, 3180, 3080, 1680, 1650, 1640 1610 |
| 11 | —CH$_2$SOCH$_3$ | Pale yellow powder, m.p. >250° C. | 3430, 3220, 3080, 1680, 1640 |
| 12 | tetrahydrofuran-2-yl | Yellow powder, m.p. 240° C. (dec.) | 3410, 3220, 3110, 3060, 1670, 1640 1060 |
| 13 | —N(CH$_3$)$_2$ | Pale yellow powder, m.p. 240° C. (dec.) | 3470(sh), 3410, 3230, 3100, 1650, 1630 |
| 14 | —CH$_2$O—(CH$_2$CH$_2$O)$_2$CH$_3$ | White powder, m.p. 187-189° C. (dec.) | 3420, 3230, 3140, 3080, 1670, 1630 |
| 15 | —COCH$_3$ | Pale yellow powder, m.p. 248-249° C. (dec.) | 3420, 3230, 3110, 1670, 1650 |
| 16 | —CH(OCH$_3$)$_2$ | White powder, m.p. 243-245° C. (dec.) | 3430, 3260, 3220, 3180, 3100, 1670, 1640 |
| 17 | —C(OH)(CH$_3$)$_2$ | White powder, m.p. 247-248° C. (dec.) | 3380, 3220, 3080, 1685, 1640 |
| 18 | (l)-pyrrolidin-2-yl, N-COCH$_2$OCH$_3$ | White powder, m.p. 246-248° C. (dec.) | 3400(br), 3220, 3080, 1680, 1640 |
| 19 | —CH$_2$O-(tetrahydropyran-2-yl) | White crystal. powder m.p. 246-249° C. (dec.) | 3390, 3220, 3050, 1670, 1650 |
| 20 | —CH(OH)CH$_3$ (l) | Pale yellow powder*$^2$ m.p. 224-225° C. (dec.) | 3360, 3220, 3080, 1685, 1640 |
| 21 | —CH(OH)CH$_3$ (d) | Pale yellow powder*$^3$ m.p. 232-233° C. (dec.) | 3330, 3220, 3080, 1690, 1640 |

TABLE 2-continued

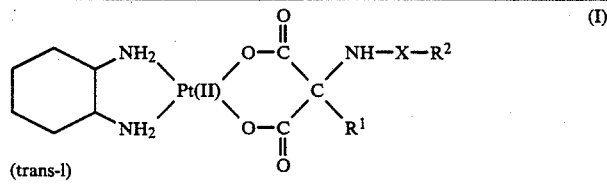

(trans-l)

(In Examples 3-26 & 28, X = CO, and in Example 27, X = SO$_2$, and in Examples 3-27, R$^1$ = H and in Example 28, R$^1$ = CH$_3$)

| Ex. No. | Complex (I)*[1] R$^2$ | Physical properties M.p., etc. | IR $\nu_{Max}^{Nujol}$ (cm$^{-1}$) |
|---|---|---|---|
| 22 | (furan ring) | Pale yellow powder, m.p. >250° C. | 3400, 3200, 3120, 1680, 1650 |
| 23 | —CH(CH$_3$)O—(tetrahydropyran) | White powder, m.p. 240–241° C. (dec.) | 3410, 3200, 3070, 1680, 1640 |
| 24 | —CH(OH)CH$_2$CH$_3$ | White powder, m.p. 227–229° C. (dec.) | 3350, 3220, 3070, 1680, 1640 |
| 25 | —CH$_2$NO$_2$ | Pale yellow powder, m.p. >250° C. | 3270, 3210, 3060, 1680, 1650, 1635 |
| 26 | —CH$_2$CON(morpholine) | White powder, m.p. 243–245° C. (dec.) | 3300, 3250, 3200, 3050, 1680, 1640 |
| 27 | —CH$_3$ | Pale yellow powder, m.p. 254–256° C. (dec.) | 3440, 3220, 3120, 1640 |
| 28 | —CH$_3$ | Pale yellow powder, m.p. 246° C. (dec.) | 3400, 3300, 3220, 3120, 1660, 1640 |

*[1] (d), (l), and (dl) mean stereoisomers (hereinafter, the same)
*[2] $[\alpha]_D^{20}$ +53.8° (c = 1.0, water)
*[3] $[\alpha]_D^{20}$ +68.2° (c = 1.0, water)

REFERENCE EXAMPLE 1

To a solution of diethyl 2-aminomalonate hydrochloride (4.2 g) and glycolic acid (1.6 g) in dimethylformamide is added triethylamine (2.12 g), and to the mixture are added 1-hydroxybenzotriazole (2.7 g) and N,N'-dicyclohexylcarbodiimide (4.33 g) with stirring under ice cooling. The mixture is reacted at 0° to 5° C. for 2 hours and further reacted at room temperature for 15 hours. The reaction mixture is concentrated under reduced pressure, and to the residue is added ethyl acetate, and the undissolved substance is filtered off. The filtrate is washed with aqueous sodium carbonate solution, dried and then the solvent is distilled off. The residue is purified by silica gel column chromatography [solvent: chloroform-ethyl acetate (2:1)] to give diethyl 2-[(hydroxyacetyl)amino]malonate (2.9 g), m.p. 74°–74.5° C.

REFERENCE EXAMPLES 2 TO 14

In the same manner as described in Reference Example 1, the corresponding starting materials are treated to give the compounds shown in Table 3.

TABLE 3

$$R^3-O-\underset{\underset{O}{\|}}{C}-\underset{H}{\overset{NH-X-R^2}{C}}-\underset{\underset{O}{\|}}{C}-O-R^4 \quad (VI)$$

(R$^3$ and R$^4$ are each ethyl, X is CO)

| Ref. Ex. No. | R$^2$ in the compound (VI) | Physical properties, etc. |
|---|---|---|
| 2 | 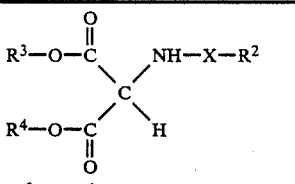 (l) | m.p. 110–111.5° C. |
| 3 | —CH$_2$OCH$_3$ | m.p. 39–40° C. |
| 4 | —CH(OH)CH$_3$ (dl) | oily substance |
| 5 | —CH(OH)CH$_2$OH | m.p. 49–52° C. |
| 6 | —CH$_2$OCH$_2$CH$_2$OCH$_3$ | oily substance |
| 7 | —CH$_2$O(CH$_2$CH$_2$O)$_2$CH$_3$ | oily substance |
| 8 | —CH(OCH$_3$)$_2$ | oily substance |
| 9 | —C(OH)(CH$_3$)$_2$ | m.p. 57–58° C. |
| 10 | —CH(OH)CH$_3$ (l) | m.p. 48–51° C. |
| 11 | —CH(OH)CH$_3$ (d) | m.p. 48–51° C. |
| 12 | —CH(OH)CH$_2$CH$_3$ | oily substance |

TABLE 3-continued $$
\begin{array}{c}
\text{R}^3-\text{O}-\overset{\overset{\displaystyle O}{\|}}{\text{C}}\diagdown\text{C}\diagup\text{NH}-\text{X}-\text{R}^2\\
\text{R}^4-\text{O}-\underset{\underset{\displaystyle O}{\|}}{\text{C}}\diagup\phantom{\text{C}}\diagdown\text{H}
\end{array} \qquad \text{(VI)}
$$

($R^3$ and $R^4$ are each ethyl, X is CO)

| Ref. Ex. No. | $R^2$ in the compound (VI) | Physical properties, etc. |
|---|---|---|
| 13 | —CH$_2$CON⟨O⟩ | m.p. 73.5–75.5° C. |
| 14 | (I)⟨pyrrolidine⟩N–COCH$_2$OCH$_3$ | oily substance |

REFERENCE EXAMPLE 15

To a suspension of 2-aminomalonic acid hydrochloride (4.2 g) in methylene chloride is added dropwise triethylamine (4.5 g). The mixture is cooled to 0° to 5° C., and thereto is added dropwise acryl chloride (1.9 g). The mixture is stirred at the same temperature for one hour and further at room temperature for 2 hours. The reaction mixture is washed with water, dried and then concentrated. The residue is recrystallized from chloroform-isopropyl ether to give diethyl 2-(acrylamino)malonate (3.1 g), m.p. 105°–106° C.

REFERENCE EXAMPLES 16 TO 21

In the same manner as described in Reference Example 15, the corresponding starting materials are treated to give the compounds shown in Table 4.

TABLE 4

$$
\begin{array}{c}
\text{R}^3-\text{O}-\overset{\overset{\displaystyle O}{\|}}{\text{C}}\diagdown\text{C}\diagup\text{NH}-\text{X}-\text{R}^2\\
\text{R}^4-\text{O}-\underset{\underset{\displaystyle O}{\|}}{\text{C}}\diagup\phantom{\text{C}}\diagdown\text{H}
\end{array} \qquad \text{(VI)}
$$

($R^3$ and $R^4$ are each ethyl, and in Reference Examples 16 to 20, X is CO, and in Reference Example 21, X is SO$_2$)

| Ref. Ex. No. | $R^2$ in the compound (VI) | Physical properties, etc. |
|---|---|---|
| 16 | —CH$_2$CH$_3$ | m.p. 89–91° C. |
| 17 | tetrahydrofuran | oily substance |
| 18 | —N(CH$_3$)$_2$ | m.p. 66–68° C. |
| 19 | —COCH$_3$ | oily substance |
| 20 | dihydrofuran | m.p. 56–58° C. |
| 21 | —CH$_3$ | m.p. 73–75° C. |

REFERENCE EXAMPLE 22

(1) Diethyl 2-aminomalonate (3.5 g) and methylsulfenylacetic acid (2.2 g) are treated in the same manner as described in Reference Example 1 to give diethyl 2-[(methylsulfenylacetyl)amino]malonate (3.6 g), m.p. 56°–58° C.

(2) To a solution of the product (2.11 g) obtained in the above (1) in methylene chloride is added m-chloroperbenzoic acid (1.7 g) under ice cooling, and the mixture is stirred at the same temperature for 20 minutes. The reaction mixture is washed, dried and then concentrated. The residue is recrystallized from chloroform-isopropyl ether to give diethyl 2-[(methylsulfinylacetyl)amino]malonate (1.7 g), m.p. 85°–87° C.

REFERENCE EXAMPLE 23

To a solution of diethyl 2-aminomalonate hydrochloride (4.2 g) and triethylamine (2.12 g) in tetrahydrofuran-methanol is added dropwise methyl isocyanate (1.25 g) at 0° to 5° C., and the mixture is stirred at room temperature for 5 hours. The reaction mixture is concentrated under reduced pressure, and to the residue is added chloroform. The organic layer is separated, washed, dried and then concentrated. The residue is recrystallized from chloroform-isopropyl ether to give diethyl 2-[(methylcarbamoyl)amino]malonate (4.2 g), m.p. 139° C.

REFERENCE EXAMPLE 24

To a solution of diethyl 2-[(hydroxyacetyl)amino]malonate (2.43 g) in methylene chloride are added dihydropyrane (1.3 g) and p-toluenesulfonic acid (20 mg), and the mixture is stirred at room temperature for 30 minutes. The reaction mixture is washed, dried and then concentrated. The residue is purified by silica gel column chromatography to give diethyl [2-[[(tetrahydropyran-2-xyloxy)acetyl)amino]malonate (2.7 g) as oily substance.

IR $\nu_{Max}^{Nujol}$ (cm$^{-1}$): 3425, 1755, 1740, 1690.

REFERENCE EXAMPLE 25

Diethyl 2-[(2-hydroxypropionyl)amino]malonate is treated in the same manner as described in Reference Example 24 to give diethyl 2-[[2-(tetrahydropyran-2-yloxy)propionyl]amino]malonate as oily substance.

IR $\nu_{Max}^{Nujol}$ (cm$^{-1}$): 3420, 1755, 1740, 1685.

REFERENCE EXAMPLE 26

(1) Diethyl 2-aminomalonate and iodoacetic acid are treated in the same manner as described in Reference Example 1 to give diethyl 2-[(iodoacetyl)amino]malonate, m.p. 96°-98° C.

(2) To a suspension of silver nitrite (4.3 g) in ether is added the product of the above (1) (4.8 g) over a period of one hour, and the mixture is stirred at room temperature under light protection for 2 days. To the reaction mixture is added ethyl acetate, and the insoluble substance is filtered off, and the filtrate is concentrated under reduced pressure. The residue is recrystallized from chloroform-isopropyl ether to give diethyl 2-[(nitroacetyl)amino]malonate (2.4 g), m.p. 118°-121° C.

REFERENCE EXAMPLE 27

To a solution of diethyl 2-acetylaminomalonate (2.17 g) in dry tetrahydrofuran is added sodium hydride (0.26 g), and the mixture is stirred at room temperature for one hour. After stirring, methyl iodide (1.60 g) is added dropwise thereto, and the mixture is stirred overnight. The reaction mixture is concentrated, and to the residue is added ethyl acetate and water. The organic layer is separated, dried and evaporated to remove the solvent. The residue is recrystallized from a mixture of isopropyl ether and n-hexane to give diethyl 2-acetylamino-2-methylmalonate (1.80 g), m.p. 89°-90° C.

What is claimed is:

1. An organic platinum complex of the formula:

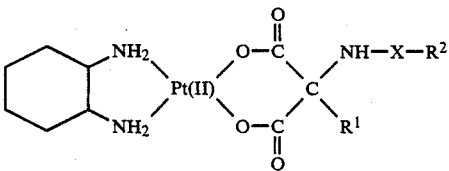

wherein $R^1$ is selected from hydrogen and lower alkyl of 1 to 3 carbon atoms, $R^2$ is selected from lower alkyl, lower hydroxyalkyl and a group of the formula: $-CH_2O(CH_2CH_2O)_mCH_3$, X is carbonyl group, m is an integer of 1.

2. The compound according to claim 1, wherein $R^2$ is an alkyl group of 1 to 3 carbon atoms or a group of the formula: $-CH_2O(CH_2CH_2O)_mCH_3$.

3. The compound according to claim 2, wherein $R^2$ is selected from methyl and methoxyethoxy-methyl.

4. The compound according to claim 3, which is [2-(acetylamino)-2-methylmalonato](trans-l-1,2-diaminocyclohexane) platinum (II).

5. The compound according to claim 3, which is [2-[(methoxyethoxyacetyl)amino]malonato](trans-l-1,2-diaminocyclohexane) platinum (II).

* * * * *